United States Patent [19]

Iino

[11] Patent Number: 4,848,905
[45] Date of Patent: Jul. 18, 1989

[54] METHOD OF AND APPARATUS FOR MEASURING SUSPENDED FINE PARTICLES

[75] Inventor: Mitsuaki Iino, Ichihara, Japan

[73] Assignee: Idemitsu Kosan Company Limited, Tokyo, Japan

[21] Appl. No.: 197,615

[22] Filed: May 23, 1988

Related U.S. Application Data

[63] Continuation of Ser. No. 868,366, May 27, 1986, abandoned.

[30] Foreign Application Priority Data

May 28, 1985 [JP] Japan ................... 60-114565

[51] Int. Cl.⁴ .................. G01N 21/05; G01N 21/49
[52] U.S. Cl. .................. 356/338; 250/574; 356/246
[58] Field of Search ........... 250/574; 356/338, 339, 356/246

[56] References Cited

U.S. PATENT DOCUMENTS

| | | |
|---|---|---|
| 3,462,608 | 8/1969 | Weston et al. |
| 3,578,867 | 5/1971 | Barrington |
| 3,953,127 | 4/1976 | Ahlquist et al. |
| 4,023,909 | 5/1977 | Ross |

FOREIGN PATENT DOCUMENTS

| | | |
|---|---|---|
| 0096420 | 12/1983 | European Pat. Off. |
| 1803728 | 8/1959 | Fed. Rep. of Germany |
| 7617247 | 5/1976 | Fed. Rep. of Germany |
| 57-42842 | 3/1982 | Japan |
| 2010479 | 6/1979 | United Kingdom |
| 8500426 | 1/1985 | World Int. Prop. O. |

Primary Examiner—Davis L. Willis
Assistant Examiner—Matthew W. Koren
Attorney, Agent, or Firm—Flynn, Thiel, Boutell & Tanis

[57] ABSTRACT

A method of and apparatus for measuring the density of fine particles floating in a fluid. The method includes the steps of: applying light to a fluid contained in a tubular member having an interior surface constituted by a mirror surface; condensing and detecting rays traveling toward one axial end of the tubular member among the light reflected by fine particles in the fluid; and subjecting the detected rays or signal to a predetermined processing, thereby measuring the density of the fine particles. The apparatus employed in this method includes: a tubular member; a light source directed in a direction perpendicular to the axial direction of the tubular member; a condenser lens disposed at one axial end of the tubular member; a detector opposing the condenser lens; and a processor which processes a signal applied thereto from the detector in a predetermined manner to obtain the density of fine particles.

8 Claims, 4 Drawing Sheets

METHOD OF AND APPARATUS FOR MEASURING SUSPENDED FINE PARTICLES

This is a continuation of Ser. No. 868,366, filed May 27, 1986, now abandoned.

BACKGROUND OF THE INVENTION

1. Field of the Invention

The present invention relates to a method of and apparatus for measuring the density of fine particles suspended in a fluid such as oil, water or air. More particularly, the present invention pertains to a method of and apparatus for optically measuring the density of fine particles suspended in such fluid.

2. Description of the Prior Art

Measurement of the density of fine particles suspended in fluids (e.g., dust and bubbles in oil, solid particles in water, or dust in air) are often effected using optical means. In these conventional optical methods, a light source, a fluid which is an object of measurement and a photodetector are disposed on a straight line so that the light from the light source is applied to the fluid, and the light having passed through the object is detected by the photodetector. Thus, the density of fine particles suspended in the fluid is measured on the basis of the fact that the quantity of light detected by the photodetector is smaller than the quantity of light emitted from the light source due to absorption or scattering of light by the fine particles.

With the above-described prior art, however, when the size and density of fine particles are small, the difference between the quantity of light from the light source and the light quantity detected by the photodetector is correspondingly small. There is, therefore, a limit in the measurable size and density of fine particles, and it has therefore been impossible to measure extremely fine particles and the density thereof. In order to obtain a required degree of accuracy in measurement, it is necessary to increase the difference between the quantity of light from the light source and that detected by the photodetector, and this involves the necessity of increasing the volume of a sample fluid as an object of measurement. An increase in volume of the sample fluid in turn causes the size of the apparatus to increase as a whole.

SUMMARY OF THE INVENTION

Accordingly, it is a primary object of the present invention to provide a method of and apparatus for measuring suspended fine particles which enable measurement of fine particles and the density thereof even when the size and densiry of the particles are extremely small, the method permitting a reduction in the overall size of the apparatus, and thus allowing the apparatus to be easily handled and readily carried.

To this end, the present invention provides a method comprising the steps of: applying light to a fluid including fine particles suspended therein; propagating this light though the fluid while reflecting the light by a mirror surface; and condensing and detecting rays traveling in a predetermined direction among the light reflected and scattered by the fine particles in the course of the propagation, thereby measuring the density of the fine particles.

By reflecting the light by means of a mirror surface, the optical path is lengthened, and this allows the fine particles to be irradiated with light from a multiplicity of directions, so that it is possible to increase the intensity of the rays condensed and thereby detected.

The present invention also provides an apparatus for realizing the above-described method, the apparatus comprising: fluid containing means having an inner surface constituted by a mirror surface and containing a fluid including fine particles suspended therein, the means being elongated in the axial direction thereof; a light source provided on the fluid containing means so that the optical axis of the light from the light source intersects the axis of the containing means at a predetermined angle; a condenser lens for condensing rays traveling in a direction parallel with the axial direction of the containing means among the light reflected and scattered by the fine particles; a photodetector disposed in opposing relation to the condenser lens; and a signal processor for processing a signal related to the quantity of light detected by the photodetector to obtain the density of the fine particles in the fluid.

DETAILED DESCRIPTION OF THE PREFERRED EMBODIMENT

Figure 1:
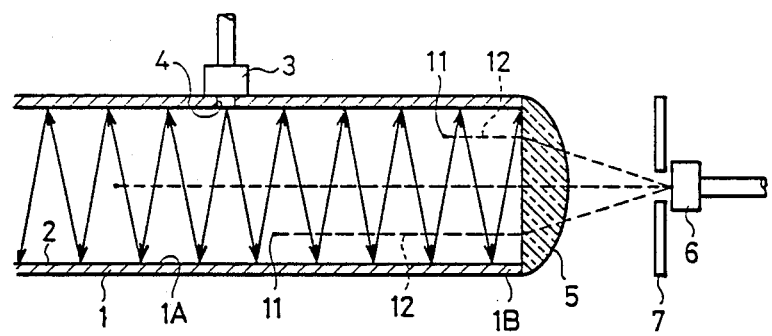
FIG. 1 is a sectional view showing the basic structure of an apparatus for carrying out the method according to the present invention.

The present invention will be described hereinunder in detail by way of embodiments in which the same members are denoted by the same reference numerals for easy understanding and explanatory convenience.

Figure 2:
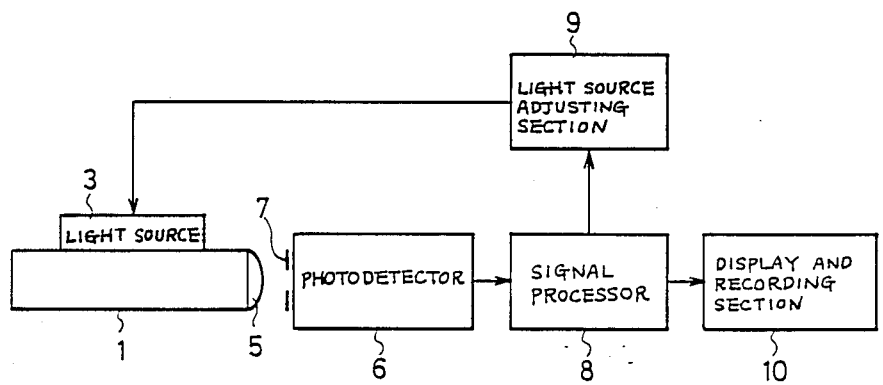
FIG. 2 is a block diagram showing the electric circuit configuration of the apparatus.

FIG. 1 is a sectional view showing the basic structure of an apparatus for carrying out the method according to the present invention, and FIG. 2 is a block diagram of the electric circuit configuration of the apparatus.

Referring first to FIG. 1, a tubular member 1 which serves as a fluid containing means for containing a fluid including fine particles suspended therein has the same inner diameter from one axial end thereof to the other, the inner surface 1A of the member 1 being constituted by a mirror surface 2. This mirror surface 2 is formed by depositing Al, Mg, Ag, Au, Cr or the like on the inner surface 1A by evaporation or plating. A light source 3 is mounted on the tubular member 1 so that the light emitted from the light source 3 is able to enter the inside of the tubular member 1 through a through-hole 4 provided in the peripheral wall of the member 1. A transparent member such as glass is fitted in this through-hole 4, thus keeping the tubular member 1 airtight. The light source 3 is disposed so that the optical axis of the light therefrom intersects the axis of the tubular member 1 at a predetermined angle greater than zero. In this embodiment, the optical axis and the axis of the member 1 intersect each other at right angles.

The light source 3 is constituted by, e.g., a photodiode or a tungsten lamp. The light source 3 is, however, not necessarily limited thereto, and may be constituted by a device which generates a laser beam or dispersed light, or may make use of an optical fiber.

A condenser lens 5 is disposed at one open end 1B of the tubular member 1. This lens 5 is a planoconvex lens which is secured to the tubular member 1 in such a manner that the the convex surface thereof faces outward and the flat surface thereof is in close contact with the open end 1B. A photodetector 6 is provided outside the condenser lens 5. The lens 5 and the photodetector 6 are disposed in opposing relation to each other on the prolongation of the axis of the tubular member 1, the distance between the lens 5 and the photodetector 6 being the same as the focal length of the lens 5. A slit member 7 is disposed between the condenser lens 5 and the photodetector 6.

The photodetector 6 is constituted by a photosensor, e.g., a multiplier phototube, CdS and so forth. The photodetector 6 is not necessarily limited to these photosensors and may be arranged such that the light condensed by the lens 5 is led into another photodetector or spectroscope through an optical fiber.

As shown in FIG. 2, a signal processor 8 is connected to the photodetector 6. Thus, the light detected by the photodetector 6 is photoelectrically converted into an electric signal and output to the signal processor 8 where it is processed as desired. The signal processor 8 has the following various functions. Namely, it serves to amplify the electric signal, to arithmetically process the amplified signal so as to obtain the density of fine particles, and to control, when the quantity of light detected by the photodetector 6 is relatively small, a light source adjusting section 9 so that the quantity of light emitted from the light source 3 is increased. A display and recording section 10 is connected to the signal processor 8. This section 10 serves to effect digital or analog display of the density of fine particles obtained by the signal processor 8 and also functions as a recorder for recording to measured density.

OPERATION

The following is a description of the operation of the above-described arrangement.

A fluid is contained inside the tubular member 1. Any type of fluid, e.g., oil, water and air, may be employed, provided that the fluid includes fine particles the density of which is to be measured, such as dust. When the light source 3 is made to emit light, the fluid is irradiated with this light. The light travels through the fluid while being reflected by the mirror surface 2. In the course of this travel, the light collides against fine particles 11 and are thereby reflected and scattered. The reflection and scattering take place for each of the fine particles 11. Rays 12 traveling in a direction parallel with the axial direction of the tubular member 1 among the scattered light are led out of the tubular member 1 while being condensed by the condenser lens 5.

In the above-described arrangement, the optical path is lengthened by virtue of the reflection effected by the mirror surface 2, and the light travels in an arbitrary direction due to the irregular reflection. Therefore, the fine particles 11 are irradiated with light from a multiplicity of directions. In other words, it is possible to obtain the same effect as that the whole of the inner surface 1A of the tubular member 11 serves as a light-emitting surface. Accordingly, the intensity of the parallel rays 12 is increased, and the quantity of the light switch is condensed by the lens 5 and detected by the photodetector 6 is increased correspondingly.

The photodetector 6 generates an electric signal on the basis of the quantity of light detected thereby. This signal is processed by the signal processor 8, and the density of the fine particles is displayed and recorded by the display and recording section 10. Even when the size of the fine particles 11 is extremely small, it is possible to measure these fine particles 11 since the intensity of the parallel rays 12 is increased by virtue of the arrangement in accordance with the present invention. Similarly, even when the density of the fine particles 11 suspended in the fluid is relatively low, it is possible to measure this density since the intensity of the parallel rays 12 generated by the fine particles 11 is favorably large. Thus, it is possible to obtain a higher measuring sensitivity than that of the conventional apparatuses.

The external shape of the apparatus according to the present invention is mainly determined by the tubular member 1, and the apparatus, therefore, has an axially elongated tubular shape as a whole even if the photodetector 6, the slit member 7 and so forth are included. Accordingly, it is possible to reduce the size and weight of the apparatus, so that the handling and operation of the apparatus are facilitated, and the apparatus is allowed to be portable.

Figure 3:
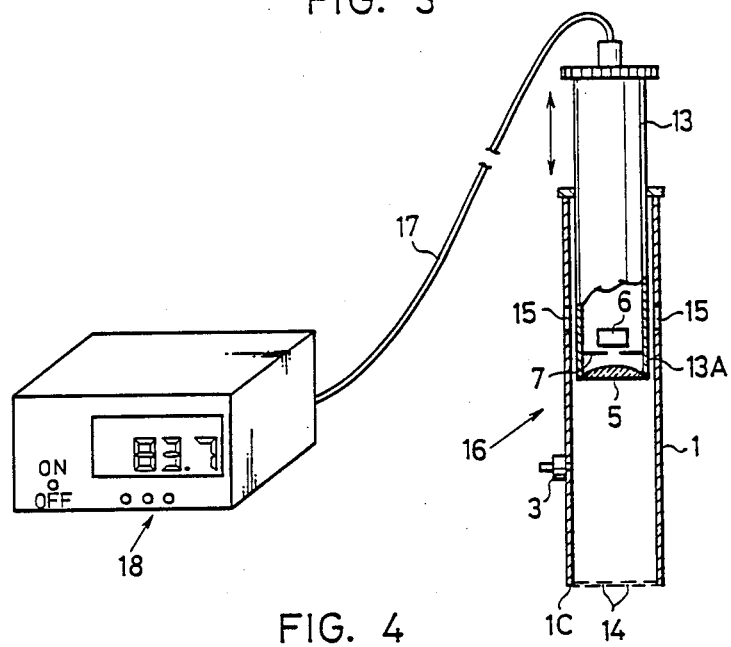
FIG. 3 is a partly-sectioned illustrative view of one practical embodiment of the apparatus according to the present invention.
Figure 4:
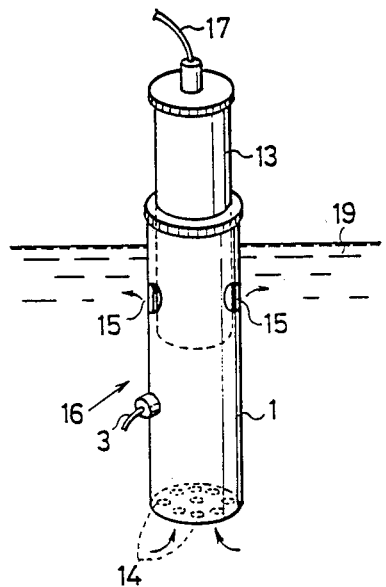
FIG. 4 is a perspective view of the detecting unit shown in FIG. 3 in an operative state.

FIGS. 3 and 4 show in combination a practical embodiment of the present invention. The tubular member 1 is provided with a cylindrical retainer member 13. The retainer member 13 serves as an inner tube with respect to the tubular member 1 which serves as an outer tube, and is therefore slidable in the axial direction of the tubular member 1. The condenser lens 5 is mounted and retained at the open end 13A of the retainer member 13 which extends inside the tubular member 1. The photodetector 6 and the slit member 7 are disposed inside the retainer member 13. Accordingly, the condenser lens 5, the photodetector 6 and the slit member 7 are movable relative to the tubular member 1. Openings 14 are provided in the bottom 1C of the tubular member 1, and openings 15 are also provided in the peripheral wall of the tubular member 1.

The tubular member 1, the retainer member 13 and so forth constitute in combination a detecting unit 16. This unit 16 is connected to an electric control unit 18 through a cord 17, the unit 18 including the signal processor 8, the light source adjusting section 9 and the display and recording section 10.

When the apparatus is not used, the retainer member 13 is telescoped into the tubular member 1. Accordingly, the detecting unit 16 is contracted, and this reduction in the length of the unit 16 enables a decrease in the space required for accommodating the apparatus. When the apparatus is to be used, the detecting unit 16 is inserted into a fluid 19, as shown in FIG. 4. At this time, the retainer member 13 is expanded with respect to the tubular member 1. In consequence, the fluid 19 enters the tubular member 1 through the openings 14, and the air is expelled from the tubular member 1 through the openings 15, whereby the tubular member 1 is filled with the fluid 19. The light source 3 is then made to emit light, and the density of fine particles suspended in the fluid 19 is thereby measured.

In this measuring operation, when the quantity of light detected by the photodetector 6 is relatively small because the density of the fine particles is relatively low, the retainer member 13 is expanded with respect to the tubular member 1 in order to increase the amount of the fluid 19 contained in the tubular member 1. In consequence, the number of fine particles in the tubular member 1 increases, and the quantity of light detected by the photodetector 6 increases correspondingly. Since, in this embodiment, the retainer member 13 is movable relative to the tubular member 1, the amount of the fluid 19 which is to be contained in the tubular member 1 can be adjusted in accordance with the density of the fine particle, so that it is possible to measure even a low density of fine particles which cannot be measured by the conventional apparatuses.

Figure 5:
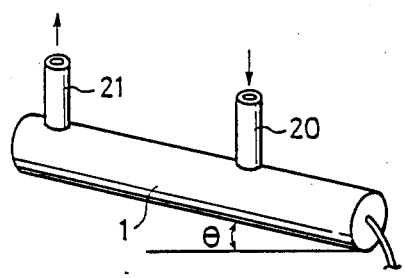
FIG. 5 is a perspective view of another embodiment of the appartus according to the present invention.

FIG. 5 shows another practical embodiment of the present invention in which a sample fluid is poured into the tubular member 1 by a manual operation. Two pipe members 20 and 21 project upwards from the peripheral surface of the tubular member 1. The tubular member 1 is inclined at an angle θ with respect to the horizontal direction, and a fluid is poured into the tubular member 1 through the lower pipe member 20, while air is expelled from the tubular member 1 through the higher pipe member 21.

Figure 6:
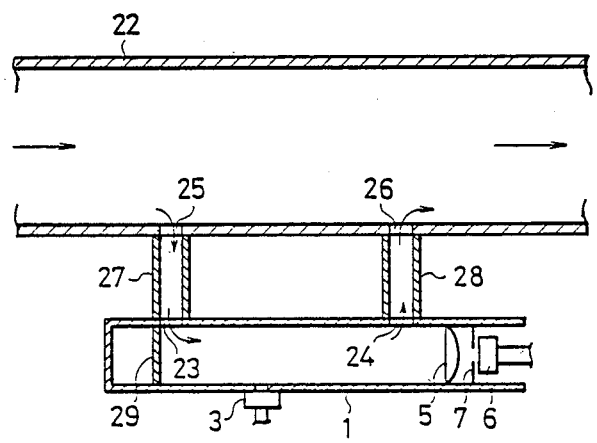
FIG. 6 is a sectional view of a still another embodiment of the apparatus according to the present invention.

FIG. 6 shows still another practical embodiment in which the density of fine particles contained in a fluid which is flowing through a pipe line 22 is directly measured. Two openings 23 and 24 are provided in the peripheral wall of the tubular member 1. The openings 23 and 24 are respectively connected through connecting pipes 27 and 28 to openings 25 and 26 provided in the pipe line 22 so that a part of the fluid flowing through the pipe line 22 makes a detour through the tubular member 1. In this embodiment, a reflection preventing member 29 is provided inside the tubular member 1, and at least the surface of the member 29 which opposes the condenser lens 5 is blackened. Thus, rays which are to be reflected by the end portion of the tubular member 1 after traveling in a direction opposite to the condenser lens 5 are absorbed by the reflection preventing member 29 and thereby prevented from being reflected. Accordingly, the parallel rays 12 scattered by the fine particles 11 and travelling toward the condenser lens 5 alone are detected by the photodetector 6, so that it is possible to increase the degree of accuracy in measuring the density of fine particles.

Figure 7:
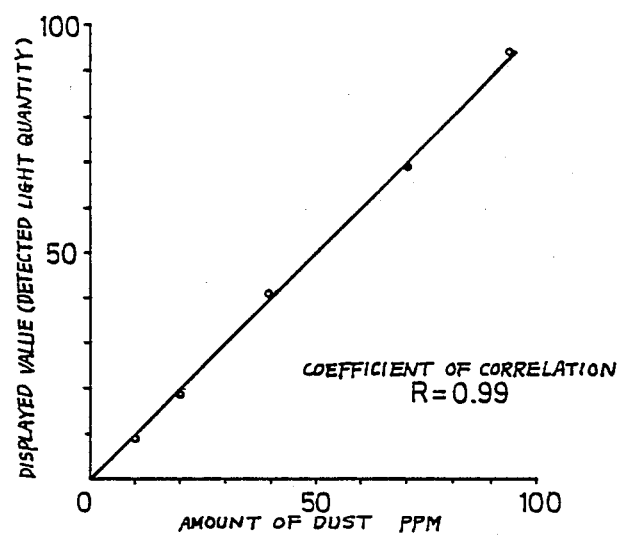
FIG. 7 is a graph showing results of an experiment.

FIG. 7 is a graph showing the results of an experiment in which JIS (Japanese Industrial Standard) dust was added to a lubricating oil to examine the correlation between the displayed value (detected light quantity) and the amount of dust according to the NSA rating mentioned in JIS B 9930-5 "Automatic Particle Instrumentation" by the contamination measuring instrument HIAC PC-320 (manufactured by HIAC/RYCO Instrument Division). As will be understood from the graph, the results showed an excellent coefficient of correlation R, i.e., R=0.99.

In another experiment, kaolin was added to water which had been distilled and filtered by a 0.8-micron Millipore filter (manufactured aby Millipore Corp.), and the correlation between the amount of kaolin particles and the displayed value (detected light quantity) was examined. The experiment also showed an excellent result.

In still another experiment, cigarette smoke in the air was employed as a sample fluid, and the correlation between the degree of dilution of the smoke and the displayed value (detected light quantity) was examined. The results showed an excellent coefficient of correlation.

Figure 8:
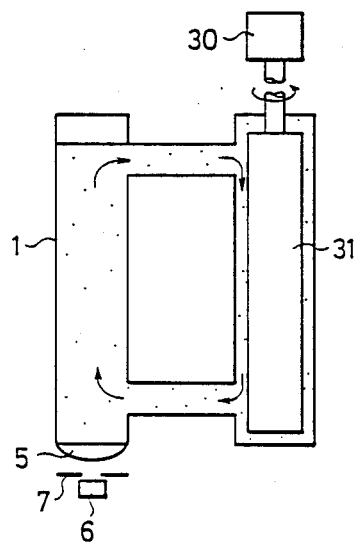
FIG. 8 shows a method of experiment for making comparison between the method of the present invention and a conventional method.
Figure 9:
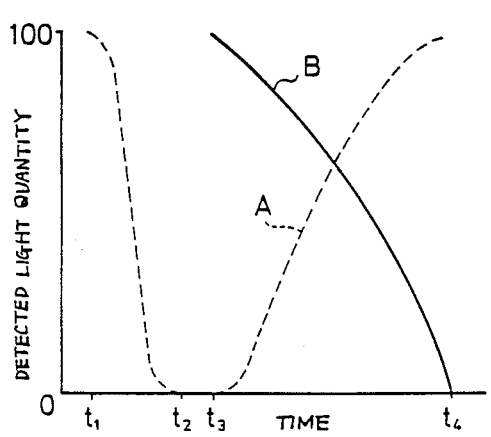
FIG. 9 is a graph showing the results of the experiment by the method shown in FIG. 8.

FIG. 9 is a graph showing the results of an experiment in which water was stirred from time $t_1$ to $t_2$ by a stirring member 31 rotated by a motor 30 in the manner shown in FIG. 8, and the density of bubbles in the water was measured by a conventional optical method and the method according to the present invention to examine the difference between the two methods in terms of the quantity of light detected. After the stirring had been stopped, the quantity of light detected by the conventional method increased with the time as shown by the curve A, whereas the quantity of light detected by the method of the invention decreased with the time as shown by the curve B.

Although the tubular member 1 is in the shape of a cylinder having a circular cross-section in each of the embodiments shown in FIGS. 1 to 6, the cross-sectional configuration of the member 1 is not necessarily limited to the circular shape, and the member 1 may have, e.g., a square cross-section. The arrangement in which the tubular member 1 is provided with a movable retainer member 13 so as to adjust the volume of the fluid contained in the tubular member 1 in accordance with the density of particles as in the embodiment shown in FIGS. 3 and 4 may also be applied to each of the embodiments respectively shown in FIGS. 5 and 6. The arrangement in which the reflection preventing member 29 is provided as in the embodiment shown in FIG. 6 may also be applied to the embodiment shown in FIGS. 3 and 4 and to the embodiment shown in FIG. 5. When the reflection preventing member 29 is applied to the embodiment shown in FIGS. 3 and 4, two reflection preventing members 29 each provided with a plurality of bores are employed and disposed at the bottom 1C of the tubular member 1 in such a manner that the bores in one member 29 and those in the other member 29 are offset from each other, whereby a fluid is allowed to enter the tubular member 1 through the bores and, at the same time, light rays can be absorbed by the reflection preventing members 29.

According to the present invention, the intensity of rays which are scattered by fine particles and detected by the photodetector is increased, so that it becomes possible to measure even fine particles which have a relatively small size and a relatively low density, and the measuring sensitivity is improved. In addition, the size of the apparatus can be reduced as a whole, so that the apparatus is allowed to be portable, and the handling and operation of the apparatus are facilitated.

What is claimed is:

1. A method of measuring suspended fine particles in a fluid, comprising the steps of:
    introducing said fluid including fine particles into an elongated container means elongated in a predetermined direction, said container means having a cylindrically shaped inner surface and means defining a cylindrical mirror surface thereon;
    applying light to said fluid in said container means along an axis that is at a predetermined angle greater than zero to a longitudinal axis of said container means;
    propagating this light through said fluid in an axial direction of said container means caused by a scattering of light by said fine particles in all directions and a reflecting of said light reaching said cylindrically shaped mirror surface;

condensing and detecting the whole of those rays traveling in a direction parallel to said longitudinal axis of said container means among the light reflected and scattered by said fine particles in the course of the propagation; and measuring the density of said fine particles in said fluid by noting the difference between the quantity of light applied to said fluid and the quantity of light detected.

2. A method according to claim 1, wherein said predetermined angle is 90 degrees.

3. A method according to claim 1, wherein the quantity of light which is applied to said fluid is variable in accordance with the quantity of condensed and detected light.

4. A method according to claim 1, wherein the amount of said fluid as an object of measurement is variable.

5. An apparatus for measuring suspended fine particles in a fluid, comprising:

a tubular fluid container member having an inner surface and means defining a cylindrical mirror surface on said inner surface and containing said fluid therein, said container member being axially elongated in a predetermined direction;

a retainer member mounted inside said tubular container member and is supported for movement axially of said container member;

a light source provided such that the optical axis thereof intersects the axis of said fluid container member at a predetermined angle greater than zero so that light from said light source will be reflected by said cylindrical mirror surface along the length of said container member;

a lens on said retainer member for condensing rays traveling in a direction parallel with the axial direction of said fluid container member among the light reflected by said cylindrical mirror surface and the light scattered by said fine particles, said lens defining an end wall of said retainer member and opposing an end wall of said tubular container member;

a photodetector means disposed in opposing relation to said condenser lens for detecting the quantity of light scattered by said fine particles in said fluid, said photodetector being housed in said retainer member; and a signal processor for processing a signal related to the quantity of light detected by said photodetector to obtain the density of said fine particles in said fluid, whereby a movement of said lens toward and away from said end wall of said tubular container member controls the volume of fluid between said lens and said end wall of said container member and the quantity of light detected by said photodetector means.

6. An apparatus according to claim 5, wherein said predetermined angle between said light source and said axis of said container member is a right angle.

7. An apparatus according to claim 5, wherein a reflection preventing member is provided at one end of said tubular fluid container member.

8. An apparatus according to claim 5, wherein circulation means are provided for circulating said fluid container in said tubular fluid container member.

* * * * *

UNITED STATES PATENT AND TRADEMARK OFFICE
CERTIFICATE OF CORRECTION

PATENT NO. : 4 848 905
DATED : July 18, 1989
INVENTOR(S) : Mitsuaki IINO

It is certified that error appears in the above-identified patent and that said Letters Patent is hereby corrected as shown below:

Column 8, line 32; delete "con-".

Column 8, line 33; change "tainer" to ---contained---.

Signed and Sealed this

Eleventh Day of September, 1990

Attest:

HARRY F. MANBECK, JR.

Attesting Officer — Commissioner of Patents and Trademarks